United States Patent [19]

Chen et al.

[11] Patent Number: 5,299,572
[45] Date of Patent: Apr. 5, 1994

[54] BIOLOGICAL ELECTRODE ARRAY

[75] Inventors: Yunquan Chen; Charles A. Laszlo; Cecil Hershler, all of Vancouver, Canada

[73] Assignee: University of British Columbia, Vancouver, Canada

[21] Appl. No.: 969,458

[22] Filed: Oct. 30, 1992

[51] Int. Cl.$^5$ .............................................. A61B 5/0492
[52] U.S. Cl. .................................................. 128/639
[58] Field of Search .............................. 128/639–644, 128/786, 733, 802; 607/116, 122, 149

[56] References Cited

U.S. PATENT DOCUMENTS

| | | | |
|---|---|---|---|
| 3,620,208 | 11/1971 | Higley et al. | 128/639 X |
| 3,882,846 | 5/1975 | Fletcher et al. | 128/2.06 E |
| 4,574,814 | 3/1986 | Buffet | 128/786 |
| 4,685,466 | 8/1987 | Rau | 128/639 |
| 4,706,679 | 11/1987 | Schmidt et al. | 128/639 |
| 4,920,968 | 5/1990 | Takase | 128/639 |
| 4,969,468 | 11/1990 | Byers et al. | 128/642 |
| 5,038,782 | 8/1991 | Gevins et al. | 128/644 |

FOREIGN PATENT DOCUMENTS

| | | |
|---|---|---|
| 3025955 | 1/1982 | Fed. Rep. of Germany . |
| 2446001 | 9/1980 | France ............................ 128/786 |
| 1551345 | 3/1990 | U.S.S.R. ............................ 128/639 |
| 1556749 | 7/1976 | United Kingdom . |

OTHER PUBLICATIONS

James et al, "Carbon Fibre Microelectrodes", J. Neuroscience Methods, 1, No. 3, 1979, pp. 279–287.

Elden, Harry R., "Biophysical Properties of the Skin", New York: Wiley-Interscience [1971] pp. 513–550.

Reucher et al., "Spatial Filtering of Noninvasive Multielectrode EMG: Part 1-Introduction to Measuring Technique and Applications", IEEE Transactions on Biomedical Engineering, vol. BME-34, No. 2, Feb. 1987.

Masuda et al., "Topographical Map of Innervation Zone Within Single Motor Units Measured with a Grid Surface Electrode", IEEE Transactions on Biomedical Engineering vol. 35, No. 8, Aug. 1988.

Primary Examiner—Lee S. Cohen
Attorney, Agent, or Firm—Norman M. Cameron

[57] ABSTRACT

A biological electrode array connects electrical apparatuses to the skin surface of a living body. The array includes an insulating mount having a central area. A case is connected to the mount and has a cavity with conductive shielding extending thereabout. A plurality of shielding electrodes extend from the insulating mount and are spaced-apart about the central area. The shielding electrodes are electrically connected to the shielding of the case. A plurality of spaced-apart brush-tip electrodes extend from the central area of the mount. Signal buffers within the cavity of the case are electrically connected to the brush-tip electrodes. Conductors extend from the cavity, each conductor being electrically connected to one of the buffers. The brush-tip electrodes have thin, but resilient wires, typically of hard stainless steel or tungsten.

13 Claims, 3 Drawing Sheets

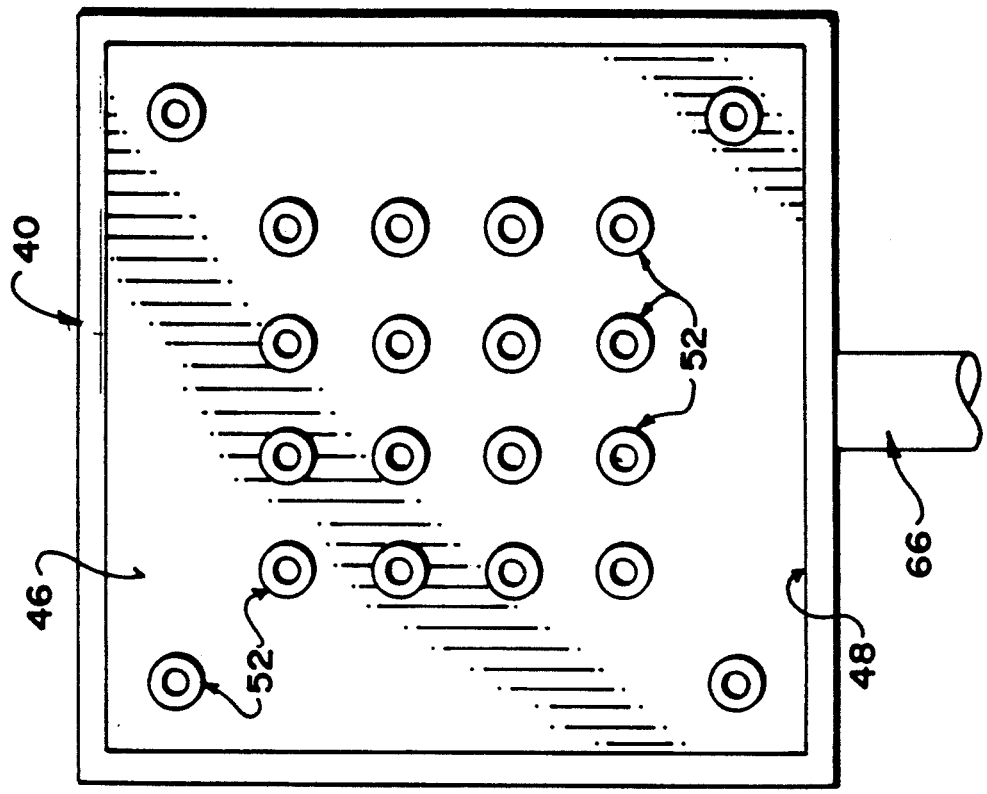
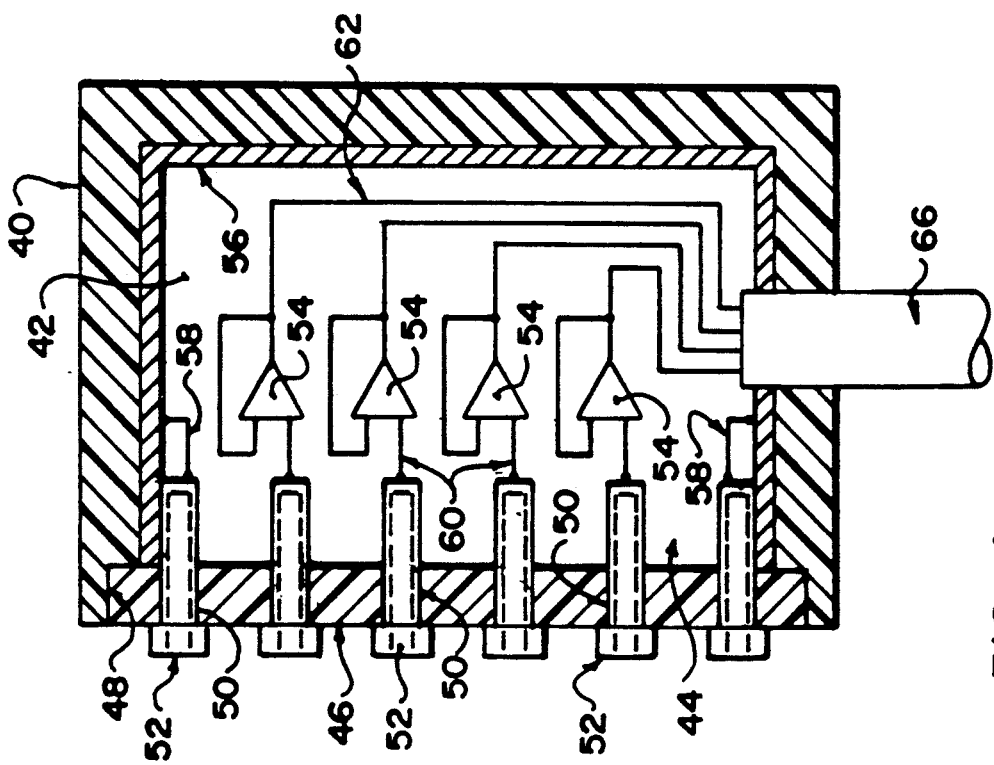
FIG. 5
FIG. 4

BIOLOGICAL ELECTRODE ARRAY

BACKGROUND OF THE INVENTION

1. Field of the Invention

This invention relates to electrode apparatuses used in detecting bioelectric signals on a living body, especially for use in detecting electromyographic (EMG) signals from the skin surface of a human body.

2. Description of Related Art

Electrodes which are conventionally used for the acquisition of EMG signals are either invasive (needle or wire) electrodes which penetrate through the skin into a muscle, or non-invasive surface electrodes which are placed on the skin surface above a muscle. Surface electrodes are preferred for their non-invasive characteristics, but their usefulness is limited. One of the reasons for this is that they pick up concurrent activities of many muscle fibres, yielding complex action potentials which represent summated or averaged activities. Reportedly EMG signals can be obtained selectively from the skin surface, i.e. action potentials of muscle fibres of individual or a small number of motor units can be obtained with appropriate combinations of several surface electrodes. The structural and dynamic properties of a muscle are detectable with use of groups of similar electrodes appropriately combined. Many basic electrodes are usually combined at fixed distances from each other in one or two dimensions and are conventionally called an electrode array.

The basic electrodes which form the array must have small contact areas with the skin. Pin electrodes with flat tips have been used in the past in the construction of arrays. However such electrodes have not been very successful because the skin-electrode impedance is too high. Pin electrodes with sharp tips have also been used to investigate the skin electrode impedance with different penetrating depths of the needle point into the skin. The results indicate that the deeper the penetrating depth, the lower the skin-electrode impedance.

U.S. Pat. No. 4,685,466 discloses a quasi-invasive needle-like electrode which penetrates into the upper, most largely cast-off cell layers of the horny skin to reduce the skin electrode impedance in a very small contact area. Since the contact area between the electrode and the skin is so small, a minimum depth of penetration must be achieved by the electrode in order to reduce the skin-electrode impedance to an acceptable level. On the other hand, the depth must be limited to the thickness of the layer of the stratum corneum of skin (from less than 50 to over 350 micrometers on human skin) in order to keep the electrode non-invasive. However it is difficult or at least inconvenient to determine and control the depth of the penetration of such an electrode in practice, especially when the electrode is part of an array and when motion occurs on the skin or in the muscle. In addition, regular electrolytic treatment is also necessary for electrodes of such small contact area to reduce the impedance of the electrodes themselves.

An example of an electrode array is found in U.S. Pat. No. 4,969,468 to Byers et al. The electrode array includes a base and a plurality of electrically conductive protuberances extending substantially perpendicular to and from the support surface of the base in a two dimensional array. Each of the protuberances has a tip for electrically contacting the tissue.

The prior art discloses various ways to improve types of biological electrodes other than those for electrode arrays suitable for EMG electrodes. Such other types typically have much larger skin contact areas (usually greater than 5 $mm^2$). An example is found in U.S. Pat. No. 3,882,846 to Fletcher. The electrode system includes an insulated electrode and an impedance transformer. Another example is found in U.S. Pat. No. 4,706,679 to Schmidt. This electrode comprises bundles of silver wire held by a conductive tube with a flat tip. These however are large area electrodes which are intended to be used individually and not in an array.

SUMMARY OF THE INVENTION

It is an object of the present invention to provide a basic electrode which has a small area of skin contact, yet has acceptable skin-electrode impedance without the need of determining and controlling the depth of penetration of the electrode into the skin.

It is another object of the invention to provide an improved electrode array which is made with this basic electrode and is easy and convenient to use.

It is a further object of the invention to provide an improved electrode array which is suitable for detecting low level bio-electric signals, especially EMG signals from the skin surface of a living body.

In accordance with these objects, the invention provides a biological electrode array for connecting electrical apparatuses to the skin surface of a living body. The electrode array includes an insulating mount having a central area. There is a plurality of spaced-apart brush-tip electrodes extending from the central area of the mount. A plurality of protrusions extend from the mount and are spaced-apart about the brush-tip electrodes. Each of the protrusions has a larger area than each of the brush-tip electrodes. The protrusions prevent the brush-tip electrodes from penetrating the skin too far.

The electrodes preferably extend further outwards from the mount as their distance from the center of the mount increases. The protrusions extend further from the mount than the electrodes. Thus the electrodes and protrusions preferably form a concave-shaped depression to conform to the shape of the living body.

Another aspect of the invention provides a biological electrode array for connecting electrode apparatuses to the skin surface of a living body. The array includes an insulating mount having a central area. A case is connected to the mount and has a cavity with conductive shielding extending thereabout. A plurality of shielding electrodes extends from the insulating mount and are spaced-apart about the central area. The shielding electrodes are electrically connected to the shielding of the case. A plurality of spaced-apart brush-tip electrodes extend from the central area of the mount. There are signal buffers within the cavity of the case. Each signal buffer is electrically connected to one of the brush-tip electrodes. Conductors extend from the cavity, each conductor being electrically connected to one of the buffers.

Preferably the electrodes have hard, resilient wires, of stainless steel or tungsten for example, which are splayed.

BRIEF DESCRIPTION OF THE DRAWINGS

FIG. 4 is a sectional view of the case for the array of FIG. 2 and internal components taken along line 3—3 of FIG. 2; and FIG. 5 is a bottom plan view of the case shown in FIG. 4.

DESCRIPTION OF THE PREFERRED EMBODIMENTS

Figure 1:
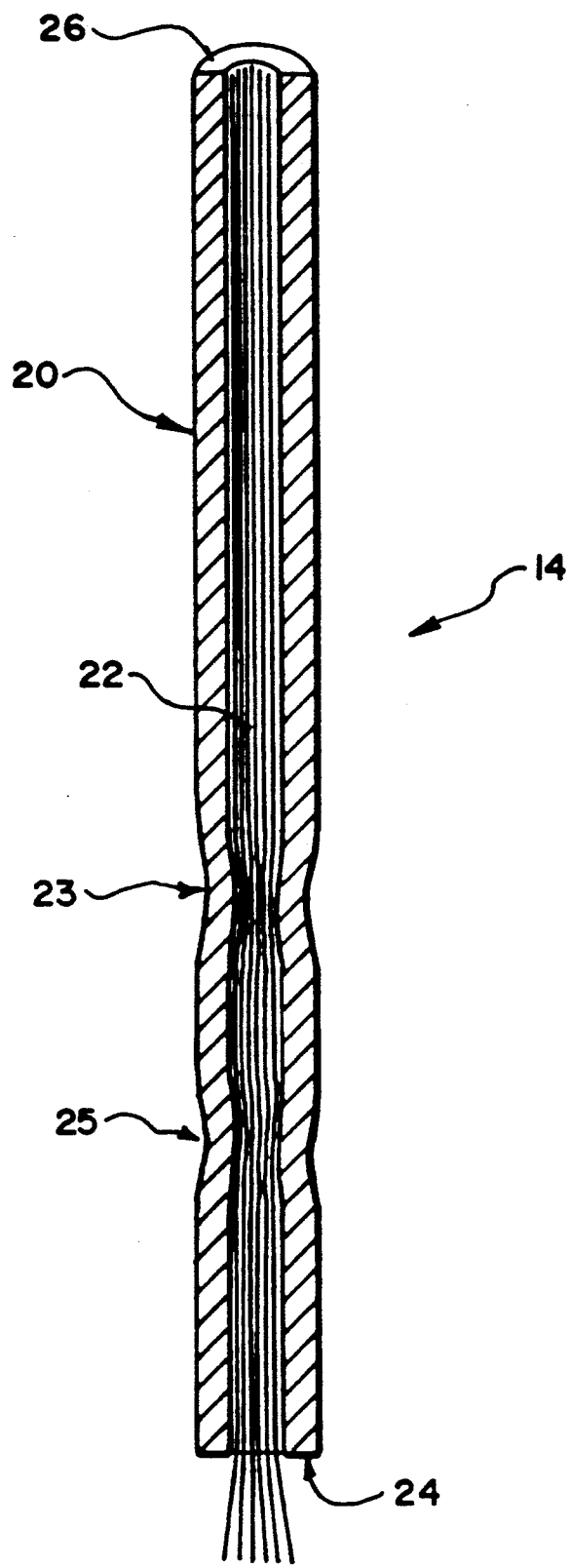
FIG. 1 is a side sectional view of a brush-tip electrode according to an embodiment of the invention.

Referring to FIGS. 2-5, an electrode array 10 includes an insulating mount 12 having a plurality of brush-tip electrodes 14 extending through apertures 16 in the mount.

In this particular example the mount 12 is rectangular and is made of a suitable insulator such as plastic. The apertures 16 extend through the mount perpendicular to its bottom surface 18. Thus the brush tip electrodes extend perpendicularly outwards from the bottom surface 18 and are parallel to each other.

As seen in better detail in FIG. 1, each brush tip electrode 14 comprises a tube 20 about 0.5 mm in diameter in this example. A medical injection needle cut to a length of 10 mm was used. The tube produced has an inside diameter about 0.25 mm. A plurality of thin but hard and resilient wires 22 extend through the tube and outwardly from its bottom 24. Thirty tungsten wires were used in this example, tungsten being preferred for its hardness and corrosion resistance in the presence of salt. High hardness stainless steel is a less expensive alternative. A suitable diameter is about 38 $\mu$m.

The fine wires are held firmly by crimping the tube at locations 23 and 25 which are about 2 mm apart. The wires are cut even with top end 26 of the tube and project 0.7-1.0 mm from the bottom 24 of the tube in this example. The wires are slightly splayed below the bottom of the tube, leaving room for individual wires to bend a bit within the elastic deformation range of the wires. This allows the lengths of the wires to adjust to fit a skin surface which is rough from a microscopic point of view. The approximate area of the brush tip is 0.05 to 0.07 mm$^2$.

Figure 2:
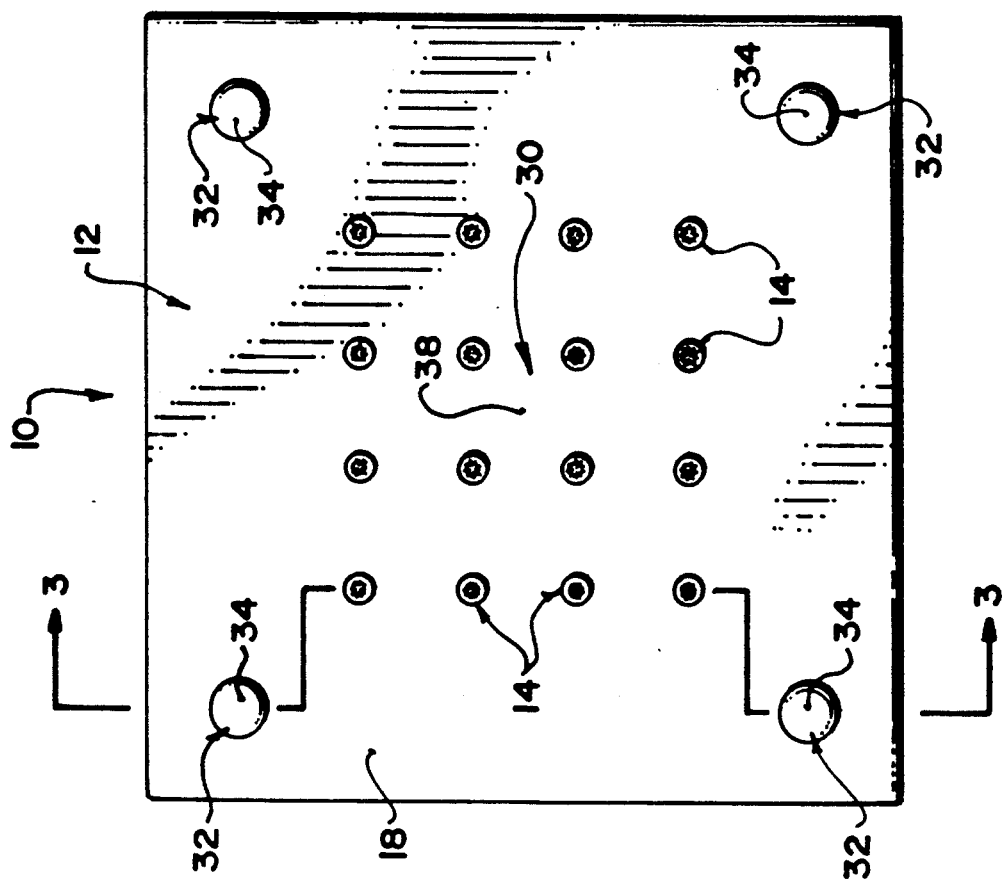
FIG. 2 is a bottom plan view of an electrode array according to an embodiment of the invention.

As seen in FIG. 2, there are sixteen brush-tip electrodes 14 in this embodiment which are arranged in a rectangular grid about the central area 30 of the insulating mount 12.

There is a plurality of shielding electrodes 32, four in this example, extending from the bottom 18 of the insulating mount which are spaced-apart about the central area and the brush-tip electrodes. As seen best in FIG. 3, each of the shielding electrodes 32 has a blade-like protrusion 34 extending outwardly from the mount and a top end 36 which forms a male electrical connector similar to tops 26 of the brush-tip electrodes.

Figure 3:
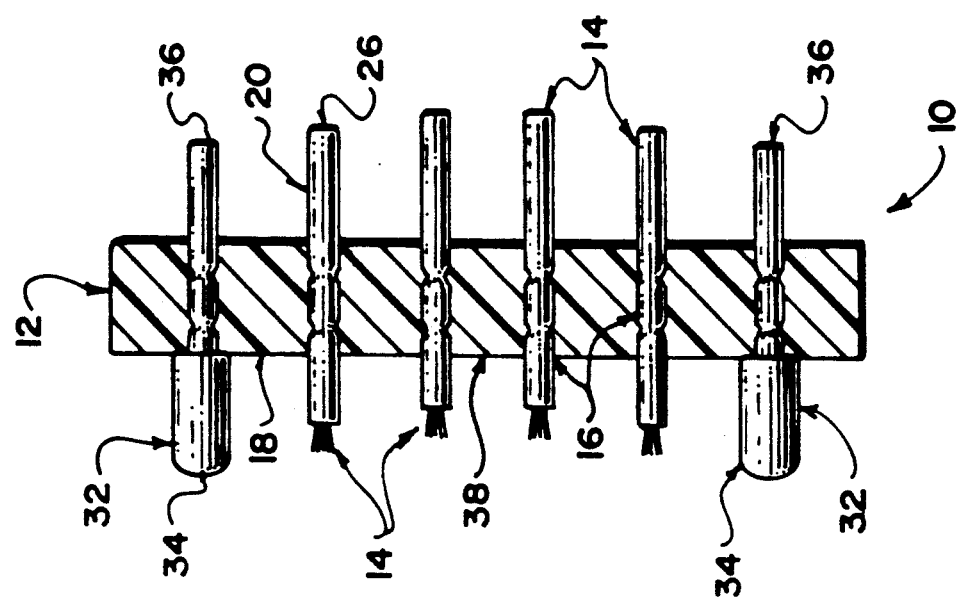
FIG. 3 is a sectional view of the base and electrodes of the array of FIG. 2 taken along line 3—3.

Mount 12 has a center 38 shown in FIGS. 2 and 3. It may be observed in FIG. 3 that the brush-tip electrodes 14 extend further outwards from bottom 18 of the mount with increasing distance from center 38 of the mount. Shielding electrodes 32 are located further outwards and extend even further from the mount. Thus, as seen best in FIG. 3, the shielding electrodes and brush-tip electrodes form a concave shape which better conforms to the living body to be fitted with the electrode array 10.

The larger shielding electrodes 32 are used for two purposes. First, they support the brush tip electrodes, preventing possible high pressure between the skin and these electrodes when the array is applied to the skin surface. Second, they connect the shielding case of the electrode array to the skin surface as described below.

The electrode array 10 also includes a case 40 which is generally box-shaped with an interior cavity 42 and an open bottom 44 provided with a cover 46. The cover fits within a rectangular recess 48 extending about the open bottom 44. The cover 46 has a plurality of apertures 50, each of which is fitted with a female electrical connector 52. There is one female electrical connector 52 positioned to correspond to each of the brush-tip electrodes 14 and shielding electrodes 32 shown in FIGS. 2 and 3. In use, the tops 26 and 36 of electrodes 14 and 32 respectively fit within the female electrical connectors 52.

A plurality of signal buffers 54 are located within cavity 42. A brush-tip electrode has an acceptable skin-electrode resistance level for a FET input amplifier to release its input bias current through the electrode, so a simple voltage follower using an operational amplifier is used as a signal buffer in this embodiment. Because no resistors, capacitors or the like are required, a large number of signal buffers can be built into the relatively small cavity 42. Building the signal buffers into the cavity of the case 40 results in a very simple and small sized electrode array.

There is an electrically conductive shielding 56 which extends about the cavity 42 inside the case 40. A suitable metal such as copper or aluminum is suitable. Conductors 58 connect the shielding to the outer female connectors 52 which connect to the shielding electrodes 32. Thus the shielding is not connected to ground, but rather to the skin surface of the living body to which the electrode array is fitted. Such skin-surface equipotential (SSEP) shielding induces less degradation to the input impedance of the signal buffers than grounded shielding. This is due to less distributed capacitive coupling between the electrode leads and the SSEP shielding. The SSEP shielding is achieved by connecting the shielding to and only to the skin surface through the female connectors and the shielding electrodes. Thus the case 40 is passively driven by the skin-surface potential. It is also possible to use a voltage follower between the skin surface and the shielding case, creating an active SSEP driver for the shielding conductor case.

Each of the signal buffers 54 is connected to one of the female connectors 52 by means of a conductor 60. As discussed, each of the inner female connectors 52 is connected to one of the brush-tip electrodes 14. Conductors 62 connect the buffers to a cable 66 extending to the electrical equipment.

The assembly comprising the electrodes 14 and 32 and the mount 12 is removably connected to the rest of the electrode array 10 by means of the male top ends 26 and 36 of the electrodes fitting within the female connectors 52. This allows the electrodes to be separated from the signal buffers for easy replacement of damaged electrodes and to allow for various configurations and shapes of electrodes to fit different skin surfaces.

Compared to a similar diameter pin electrode with a flat tip, a brush-tip electrode is as easy to deal with when applied to the skin as the flat tip electrode, but has a much lower skin-electrode impedance. A brush-tip electrode of a size suitable for forming the electrode array has the same order of skin-electrode impedance as a sharp tip pin electrode which is not convenient to use in practice. Furthermore, the brush-tip electrode has a much flatter skin-electrode impedance frequency response compared to the sharp tip pin electrode and does not require electrolytic treatment for the electrodes.

Due to the excellent performance of the brush-tip electrodes, the effective SSEP shielding and the direct connection of the electrode array to the electronics, higher quality recordings of bio-electric signals can be obtained repetitively and reliably.

When compared to the electrode of U.S. Pat. No. 4,706,679 to Schmidt, the electrodes have two different purposes. The Schmidt electrode is an EEG electrode while the present one is primarily intended as a multi-channel EMG electrode. As discussed above, the size of the electrodes is quite different and the Schmidt electrode cannot simply be downscaled. The use of thin, hard wires of hard stainless steel or tungsten which are slightly splayed gives the improved skin-electrode contact required for an array of EMG electrodes. The fine wires provide better contact with the living layer of skin under the outermost dead layer which contributes most of the skin impedance. Schmidt used thick, soft silver wire bunched together with a planar tip to avoid hurting the patient. This problem does not arise where an array of electrodes are used with much harder, but much thinner wire in the case of the present invention. The pressure of the array on the patient is distributed amongst the plurality of electrodes used (20 in the illustrated example).

It will be understood by someone skilled in the art that many of the details given above are by way of example only and are not intended to limit the scope of the invention which is to be interpreted with reference to the following claims.

What is claimed is:

1. A biological electrode array for connecting electrode apparatuses to the skin surface of a living body having a shape, the electrode array comprising:
   an insulating mount having a central area with a center therein;
   a plurality of spaced-apart brush-tip electrodes extending from the central area of the mount, the electrodes extending outwardly further from the mount as their distance from the center increases; and
   a plurality of protrusions extending from the mount further than the electrodes, the protrusions being spaced-apart about the brush-tip electrodes so the electrodes and the protrusions form a concave-shaped depression to conform to the shape of the living body, and each of the protrusions having a larger are than the brush-tip electrodes, whereby the protrusions prevent the brush-tip electrodes from penetrating the skin too far.

2. An electrode array as claimed in claim 1, wherein the protrusions are blade-shaped.

3. An electrode array as claimed in claim 1, wherein each of the brush-tip electrodes has a plurality of bunched wires.

4. An electrode array as claimed in claim 1, wherein the protrusions are electrically conductive, the array having a case connected to the mount with electrically conductive shielding, the shielding being electrically connected to the protrusions.

5. An electrode array as claimed in claim 4, wherein the array includes signal buffers inside the case, each said buffer being electrically connected to one of the brush-tip electrodes.

6. A biological electrode array for connecting electric apparatuses to the skin surface of a living body, comprising:
   an insulating mount having a central area;
   a case connected to the mount and having a cavity with conductive shielding extending thereabout;
   a plurality of shielding electrodes extending from the insulating mount and being spaced-apart about the central area thereof, the shielding electrodes being electrically connected to the shielding of the case;
   a plurality of spaced-apart brush-tip electrodes extending from the central area of the mount;
   signal buffers within the cavity of the case, each said signal buffer being electrically connected to one of the brush-tip electrodes; and
   conductors extending from the cavity, each said conductor being electrically connected to one of the buffers.

7. An electrode array as claimed in claim 6, wherein each of the brush-tip electrodes has a plurality of wires extending outwardly therefrom.

8. An electrode array as claimed in claim 7, wherein each said brush-tip electrode includes a tube, the wires extending from a first end of the tube.

9. An electrode array as claimed in claim 8, wherein each said tube has a second end with a releasable connector connecting each said brush-tip electrode to one of the signal buffers.

10. An electrode array as claimed in claim 6, wherein the signal buffers are operational amplifiers.

11. An electrode array as claimed in claim 6, wherein the shielding electrodes have outer ends which are larger than the brush-tip electrodes.

12. An electrode array as claimed in claim 6, wherein the insulating mount has a center within the central area, the brush-tip electrodes further from the center extending outwardly further than brush-tip electrodes near the center and the shielding electrodes extending outwardly further than the brush-tip electrodes.

13. A biological electrode array for connecting electric apparatuses to the skin surface of a living body, comprising:
   an insulating mount; and
   a plurality of spaced-apart brush-tip electrodes extending from the mount, each said electrode having a diameter of 38 $\mu$m and an outer end with 30 resilient, splayed wires.

* * * * *